US010737122B2

(12) United States Patent
Weidlich et al.

(10) Patent No.: US 10,737,122 B2
(45) Date of Patent: Aug. 11, 2020

(54) SELF-SHIELDED IMAGE GUIDED RADIATION ONCOLOGY SYSTEM

(71) Applicants: ETM Electromatic, Inc., Newark, CA (US); Georg Weidlich, Palo Alto, CA (US); William L. Nighan, Portola Valley, CA (US); Dennis Dore, Pleasanton, CA (US)

(72) Inventors: Georg Weidlich, Palo Alto, CA (US); William L. Nighan, Portola Valley, CA (US); Dennis Dore, Pleasanton, CA (US)

(73) Assignee: ETM Electromatic, Inc., Newark, CA (US)

( * ) Notice: Subject to any disclaimer, the term of this patent is extended or adjusted under 35 U.S.C. 154(b) by 0 days.

(21) Appl. No.: 16/060,962

(22) PCT Filed: Dec. 9, 2016

(86) PCT No.: PCT/US2016/065879
§ 371 (c)(1),
(2) Date: Jun. 11, 2018

(87) PCT Pub. No.: WO2017/100611
PCT Pub. Date: Jun. 15, 2017

(65) Prior Publication Data
US 2018/0280733 A1    Oct. 4, 2018

Related U.S. Application Data

(63) Continuation-in-part of application No. 14/634,361, filed on Feb. 27, 2015, now Pat. No. 9,661,734, which
(Continued)

(51) Int. Cl.
*A61N 5/00* (2006.01)
*A61N 5/10* (2006.01)
(Continued)

(52) U.S. Cl.
CPC ............ *A61N 5/1081* (2013.01); *A61B 6/032* (2013.01); *A61B 6/0457* (2013.01);
(Continued)

(58) Field of Classification Search
CPC ................ A61N 2005/1061; A61N 2005/1094
See application file for complete search history.

(56) References Cited

U.S. PATENT DOCUMENTS 5,548,627 A * 8/1996 Swerdloff ................ A61B 6/00
378/4
9,772,427 B2 9/2017 Kang et al.

\* cited by examiner

*Primary Examiner* — Dani Fox
(74) *Attorney, Agent, or Firm* — James E. Eakin (57) ABSTRACT

An image-guided radiotherapy system adapted to be juxtaposed adjacent a CT scanner comprises a frame having an orifice adapted to permit passage therethrough of a couch on which a patient is positioned, together with a gantry assembly rotatably mounted on the frame in which the gantry assembly comprises a shielding cylinder having an orifice therethrough in alignment with the orifice in the frame. The shielding cylinder has affixed thereto a linac-based treatment head configured to provide radiotherapy, and a beamstop positioned angularly opposite the treatment head to absorb radiation from the treatment head. The shielding cylinder provides sufficient shielding of radiation scattered from the patient and the remainder of the system to not require a conventional vault. In some embodiments an arch may be used instead of a cylinder.

20 Claims, 10 Drawing Sheets

Embodiment of an SS-HGIGRT system having stationary shielding

Related U.S. Application Data is a continuation-in-part of application No. 14/192,864, filed on Feb. 27, 2014, now Pat. No. 9,622,333.

(60) Provisional application No. 62/265,130, filed on Dec. 9, 2015.

(51) Int. Cl.
*A61B 6/00* (2006.01)
*A61B 6/03* (2006.01)
*A61B 6/04* (2006.01)

(52) U.S. Cl.
CPC .............. *A61B 6/4078* (2013.01); *A61B 6/50* (2013.01); *A61N 5/1049* (2013.01); *A61N 2005/005* (2013.01); *A61N 2005/1061* (2013.01); *A61N 2005/1094* (2013.01)

Figure 2 - Embodiment of an SS-HQIGRT system having stationary shielding

Figure 3

Figure 4 - Block diagram of an embodiment of an SS-HQIGRT system

Figure 5 – An embodiment of an SS-HQIGRT system adjacent a fan beam CT scanner with a shared couch Figure 6 -- An embodiment of an SS-HQIGRT system showing the treatment head and primary beam block mounted on a frame, with the couch of the CT scanner visible in the aperture.

Figure 7 - Perspective view of an embodiment of an SS-HQIGRT system showing the shielding arch, treatment head, beam stop, rotating frame, and shared couch

Figure 10 ically relates to radiotherapy systems that are self-shielding while capable of treating a large percentage of cancers. In an additional aspect, the present invention relates to radiotherapy systems which combine high resolution imagers, such as fan beam CT imagers, with linac-based X-ray systems.

SELF-SHIELDED IMAGE GUIDED RADIATION ONCOLOGY SYSTEM

RELATED APPLICATIONS

This application is a conversion of U.S. Patent Application Ser. No. 62/265,130, filed Dec. 9, 2015, and further is a continuation in part of PCT Application Ser. No. PCT/US15/18164 filed Feb. 27, 2015, and U.S. patent application Ser. No. 14/634,361, filed Feb. 27, 2015, which are in turn continuations-in-part of U.S. patent application Ser. No. 14/192,864, filed Feb. 27, 2014, all of which are incorporated herein by reference.

FIELD OF THE INVENTION

The present invention relates generally to radiation oncology treatment systems, and more particularly relates to radiotherapy systems that are self-shielding while capable of treating a large percentage of cancers. In an additional aspect, the present invention relates to radiotherapy systems which combine high resolution imagers, such as fan beam CT imagers, with linac-based X-ray systems.

BACKGROUND OF THE INVENTION

State-of-the-art in radiation oncology treatments use 6 MeV to 20 MeV X-ray doses from linear accelerator systems. The systems are configured to provide dose rates that allow treatment of a cancer patient in term of "fractions", which refers to the dose in any given treatment session for a patient. For example, a dose rate of 10 Gy/minute at 1 meter from the linear accelerator is used for some 6 MeV systems.

The most current linear accelerator systems, such as those from Varian, Elekta, and Accuray generally include some form of X-ray imaging as part of the system, for the purpose of providing some form of image of a patient's tumor with respect to the patient's other anatomical structures. Prior to treatment with a linear accelerator system, a standard course of the diagnosis and development of a treatment plan for a cancer patient also includes developing patient images by high quality imaging machines in order to determine the size and position of a tumor or tumors to be treated with the X-ray dose. Imaging prior to radiation treatment can be performed with dedicated imaging systems such as fan-beam CT (computed tomography) scanners, an MRI (magnetic resonance imaging) system, and/or a PET (positron emission tomography) scanner, with some PET scanners combining CT scanning within a single machine. Each imaging technique has its advantages and provides benefits in creating images that are later used for treating cancer with high energy X-rays. A further application of the fan-beam CT scanner is the ability to use a CT scan to correct for any inhomogeneity in a particular patient's tissues in order to optimize the radiation treatment plan. Thus, in a significant percentage of radiation oncology cases, a CT scan is used not only for the imaging of the tissue before treatment but also for correcting for tissue inhomogeneity in terms of Hounsfield units. These imaging techniques are well known to radiation oncologists.

State-of-the-art machines that contain linear accelerators for the purpose of generating radiation to treat the patients include imaging as well, but typically in the form of either two-dimensional X-ray imaging, or what is known as "cone beam" CT imaging. These imaging techniques provide some information, but at a generally lower image quality compared to dedicated fan beam CT scanners or MRI machines. It is technologically challenging and expensive to incorporate high quality fan beam CT scanning or MRI into a linear accelerator system. These product combinations have proven unpopular, perhaps because of the expense of not only the machine, but also the need to create a special new vault for shielding medical personnel. Radiation therapy systems generate multiple sources of unwanted radiation are produced that provide a threat to operators, workers in adjacent areas, and the public. These sources of radiation consist of primary radiation that is transmitted through the patient, scatter radiation produced by the patient tissues and parts of the Radiotherapy system that are exposed to the primary radiation, and leakage radiation from the X-ray generating and collimating components of the system.

Treatment rooms, or vaults or bunkers, used in radiation oncology include extensive shielding to protect medical personnel as well as the public from the radiation generated while treating the cancer patient. Such shielding is most often made of concrete, although lead and steel and other materials can also be used when a smaller footprint is required or when limited by external dimensions. For an energy of 6 MeV and dose of 10 Gy/min, a thickness of several feet of concrete shielding is typically used. Such vaults typically cost at least $1,000,000, or $2,000,000 or more to shield a single multi-MeV level radiation oncology system and to finish the room to a standard that is suitable for treating patients.

Because of the cost of such conventional systems, including the vault or bunker, the availability of these devices is limited. Typically, only large hospitals are able to utilize these devices often enough to justify the costs of offering such radiotherapy services. This, in turn, restricts the availability of these devices to highly populated areas. Moreover, even in highly populated areas, a group of related medical facilities will install such radiotherapy systems at only one or two of their facilities. In such instances, patients requiring radiotherapy treatment frequently are required to travel significant distances to receive their treatment. In many instances the burden of such travel is borne by the patient, but in other instances, the hospital must arrange transport of the patient to the treatment facility. These ongoing costs are significant, to say nothing of the stress on a patient who is already suffering from a serious illness.

The challenge is even greater outside of developed countries with large urban populations. There are approximately 7,600 radiotherapy facilities in the world (2300 in the USA) while approximately 60,000 CT scanners are available worldwide at facilities that provide imaging services. A reasonable assumption is that every radiotherapy facility in a developed country utilizes an average of 2.5 CT scanners. Thus, it is reasonable to estimate that there are 41,000 CT scanners in facilities that do not presently provide radiotherapy. Some, perhaps many, of these centers are in developing, rural, or under-served parts of the world. In such areas, it is reasonable to assume an average of 1.5 CT scanners per facility. From this, it can be estimated that there are over 27,000 facilities worldwide with access to CT imaging, but without radiotherapy. It is likely that, if the costs for providing radiotherapy treatments locally were manageable, such as by reducing the need for a vault, and/or reducing the cost of the radiotherapy system itself, a significant number of these facilities would seek to improve the lives of the patients in their care by installing such a radiotherapy system.

Another factor that perhaps limits the number of installations offering radiotherapy for cancer patients is the difficulty in mating high resolution images to linac-based X-ray sources. It is well understood that, for a variety of reasons, fan beam CT imagers at present offer the best spatial and contrast resolution. The greater detail offered by such imagers is significant, since such images permit the implementation of greatly improved image-guided radiotherapy, or IGRT. In conventional IGRT, a fan beam CT scan is made well in advance of the day of treatment, frequently at a different facility than where treatment will occur. Then, on treatment day, the CT-generated image is used to position the patient for treatment. However, because it has historically been difficult to combine a fan beam CT imager with a linac-based X-ray source, verification of the patient's position is made using a cone beam CT scanner. Cone beam CT scanners have thus far proven incapable of providing image quality equivalent to a fan beam CT scanner. Thus, while the lower resolution and generally inferior image quality provided by cone beam CT scanners is currently used for verification of patient position, the resulting image matching process has significant potential for error due not only to the lower quality of the day-of-treatment cone beam CT scans compared to the diagnostic fan beam CT scans, but also of the difference in time and location. Thus, the higher quality images that would be possible if the radiotherapy system comprised a fan beam CT imager integrated together with an X-ray source would plainly offer significant benefits for both the patient and the treating medical team.

Therefore, that has been a need for a radiation oncology system that combines both a true fan beam CT imager with a linac-based oncology X-ray system.

Further, there has been a need for a radiation oncology system which can be used in the treatment of a significant percentage of oncology cases, yet does not require the construction of a conventional vault.

There is a need for a novel new product for the treatment of cancer that takes advantage of high quality imaging systems that are already available, especially fan beam CT scanners.

There is a need for an X-ray linac system, capable of outputting sufficient energy for the treatment of a substantial number of cancers, for example 6 MeV, that does not require a conventional vault or bunker. The new system would be self-shielded or only require minimal and economical room modification.

There is a need for a 6 MeV X-ray linac system for the treatment of cancer that can treat as many as 90% of all types of cancers, but that costs less than 50% of existing solutions.

There is a need for a 6 MeV X-ray linac system for the treatment of cancer that is designed to work with a fan beam CT scanner, sharing a treatment couch, for the purpose of high quality imaging of the patient immediately prior to radiation treatment, which will improve accuracy of the treatment. The fan beam CT scanner may be pre-existing at a facility, before the installation of the new 6 MeV X-ray linac system.

SUMMARY OF THE INVENTION

The present invention is self-shielded image-guided radiation oncology system designed to work with fan beam CT scanners, and, in an embodiment, capable of providing 6 MeV energy levels for treatment of patients. In addition, in an embodiment the present invention is self-shielding, thus substantially if not entirely eliminating the need for a vault or bunker to be constructed. Thus, in embodiments comprising multiple aspects of the present invention, the system of the present invention can properly be described as a self-shielded, high quality image guided radiation therapy system, sometimes referred to hereinafter as an SS-HQIGRT system, although in other embodiments the invention may be thought of as comprising a self-shielded (sometimes "SS" hereinafter, for simplicity) linac-based X-ray source suitable for integration into an existing fan beam CT imaging system.

In an embodiment of a method of the present invention, fan beam CT is employed in a radiation therapy machine for its greatly improved image quality for the day-of-treatment CT, thus offering the treating medical team much greater accuracy during the process of matching diagnostic CT images to day-of-treatment images, with a resulting improvement in the accuracy of treatment delivery. In an embodiment of an aspect of the invention, the overall SS-HQIGRT system comprises a pre-existing fan beam CT scanner, already installed at the hospital or treatment center, and further comprises an SS X-ray source installed in line with that pre-existing fan beam CT. In other implementations, the SS X-ray source is installed simultaneously with a fan beam CT scanner to provide a complete SS_HQIRT system. The fan beam CT scanner may also be of the type used for simulation of radiation treatment. In such an arrangement, the fan beam CT scanner rotates around the patient at high rpms while the radiation therapy portion—the X-ray source—operates, for example, at a rotation speed of 1 rpm or 6 degrees per second, which is fast enough for radiation treatment.

While some existing systems offer energy levels as high as 18 MeV for treatment of certain cancers, an energy level of 6 MeV is sufficient for treatment of a large percentage of cancers. The energy level of 6 MeV also permits installation of the SS X-ray source without the need for a conventional vault or bunker. This permits the radiation therapy system of the present invention to be used at any hospital or facility that has or can install a fan beam CT scanner. Thus, many of the 27,000 facilities that have scanning capability can become full radiation therapy treatment centers.

To provide the self-shielding feature, the shielding material is moved relatively close to the isocenter of the radiation treatment beam as compared to conventional systems. In an embodiment, the X-ray source of the present invention comprises a "shielding ring" or "shielding arch" that blocks the entire primary radiation beam. In some embodiments, in addition to the arch, a beam stop is also used to attenuate the primary radiation beam. A conventional vault or bunker, and the associated multi-million dollar expense, is not necessary. Depending upon the embodiment, additional secondary shielding is provided by the lead-lined Linac and radiation-defining head. In some instances, as additional facility shielding can be installed, such as removable lead or steel panels, if necessary or desired.

For a conventional vault design, a primary shielding barrier covers all possible intercepts of the projected primary radiation field with the vault and therefore often requires a thickened "primary shielding belt" on the treatment room walls and the center portion of the ceiling. In the present invention, the X-ray source is designed so that this primary shielding belt can be positioned closer to the patient with the result that the total area required shielding is greatly reduced. An additional benefit provided by the use of a smaller radiation-source-to-isocenter distance than conventional linear accelerator systems is that the effective dose rate at the isocenter will increase. This permits a corresponding decrease in the utilization factor of the overall system, which in turn permits decreasing the required thickness of the primary shielding belt. For example, in an embodiment, a radiation-source-to-isocenter distance of 85 centimeters can be used. Another benefit of the present design is that the size of the treatment field can be restricted to 25 cm×25 cm at isocenter, which further decreases the required width of the primary shielding belt provided by the arch and/or beam stop. Further, unlike robotic linear accelerator systems such as the Accuray CyberKnife, the system of the present invention travels a substantially circular beam path which minimizes the area required to be covered by the primary shielding belt.

In the X-ray system of the present invention, only collimating head leakage radiation, and scatter radiation deflected from the shielding arch and from the patient and couch, establishes the need for secondary shielding. Due to the close proximity of the primary shielding arch to the isocenter, most of this secondary radiation is attenuated by the arch. Thus, only minor shielding on the external room walls is be needed in order to absorb the residual secondary radiation escaping the primary shielding arch, which permits existing facilities to be retrofitted easily to accommodate the X-ray source of the present invention. An addition feature of the present invention is that it is not necessary to couple the shielding for the linac, the shielding for the primary beam, and the shielding for secondary radiation (scattered from the patient or another element). The different shielding elements of the present invention are designed specifically for the type and location of the radiation that is to be shielded.

THE FIGURES

The foregoing and other features of the present invention can be better appreciated from the following Detailed Description of the Invention, taken together with the appended Figures, as described below.

DETAILED DESCRIPTION OF THE INVENTION

Figure 1A:
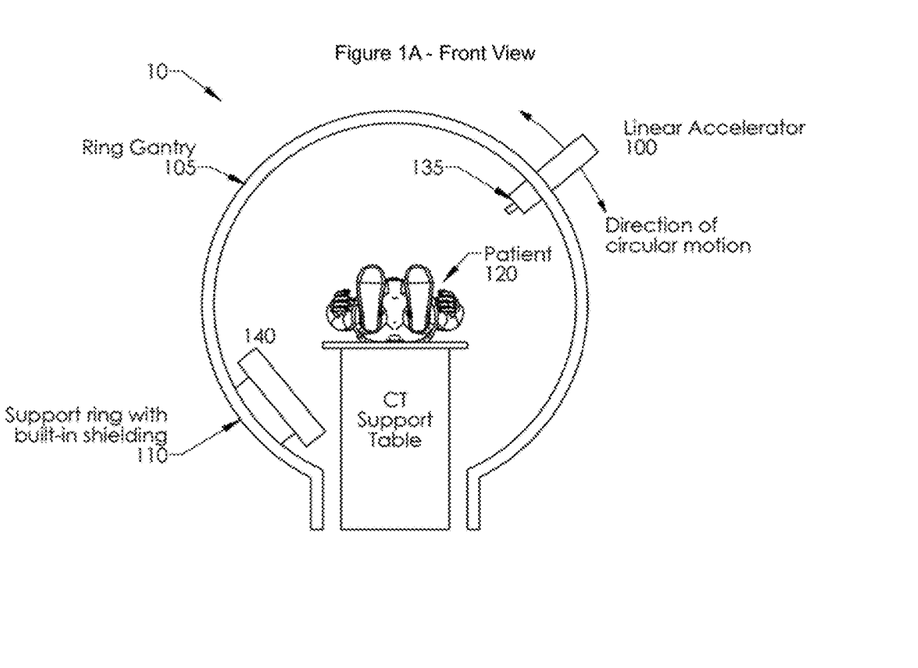
FIGS. 1A and 1B show in front elevation and side elevation views the overall design of an embodiment of an SS_HQIGRT system in accordance with the present invention.
Figure 1B:
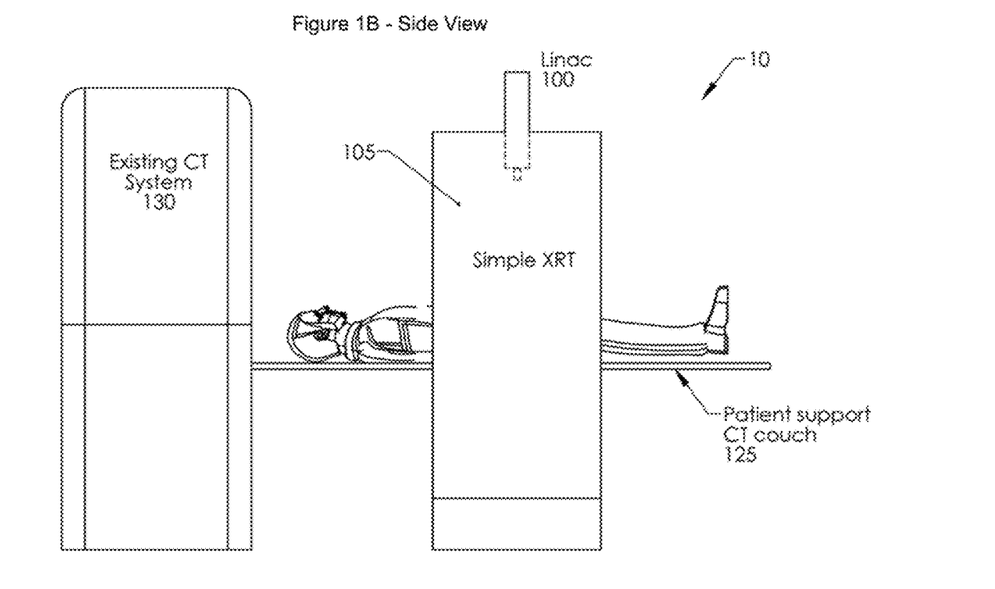
Figure 2:
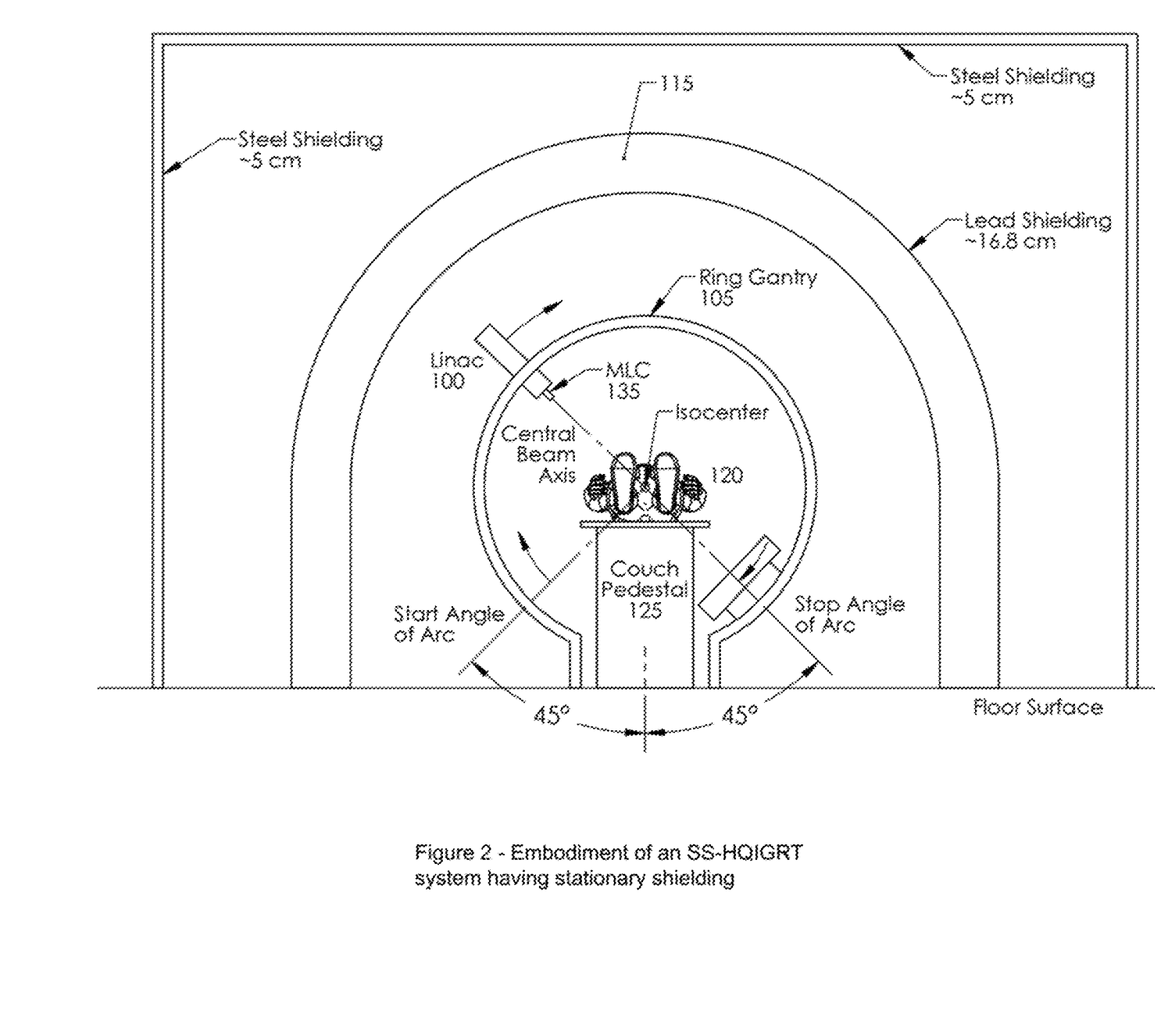
FIG. 2 is a more detailed side elevational view of the embodiment shown in FIGS. 1A-1B.

Referring first to FIGS. 1A-1B and 2, an embodiment of an SS X-ray source 10 in accordance with the present invention can be better appreciated. A linear accelerator, or linac, 100 moves around a ring gantry 105. Shielding 110 can be incorporated around the ring gantry as shown in FIG. 1A, or can be a separate arch 115 as shown in FIG. 2. The patient 120 is positioned on the CT support table, or couch, 125, and the CT imager 130 is positioned adjacent the SS X-ray source. The Linac 100 is mounted isocentrically within the ring gantry 105 and is able to rotate almost a full rotation of 360 deg. In at least some embodiments, a multi-leaf collimator 135 is incorporated into the treatment head containing the linac 100. Further, in at least some embodiments, a beam stop 140 is positioned diametrically opposite the linac 100 and rotates with the linac to provide shielding.

Figure 4:
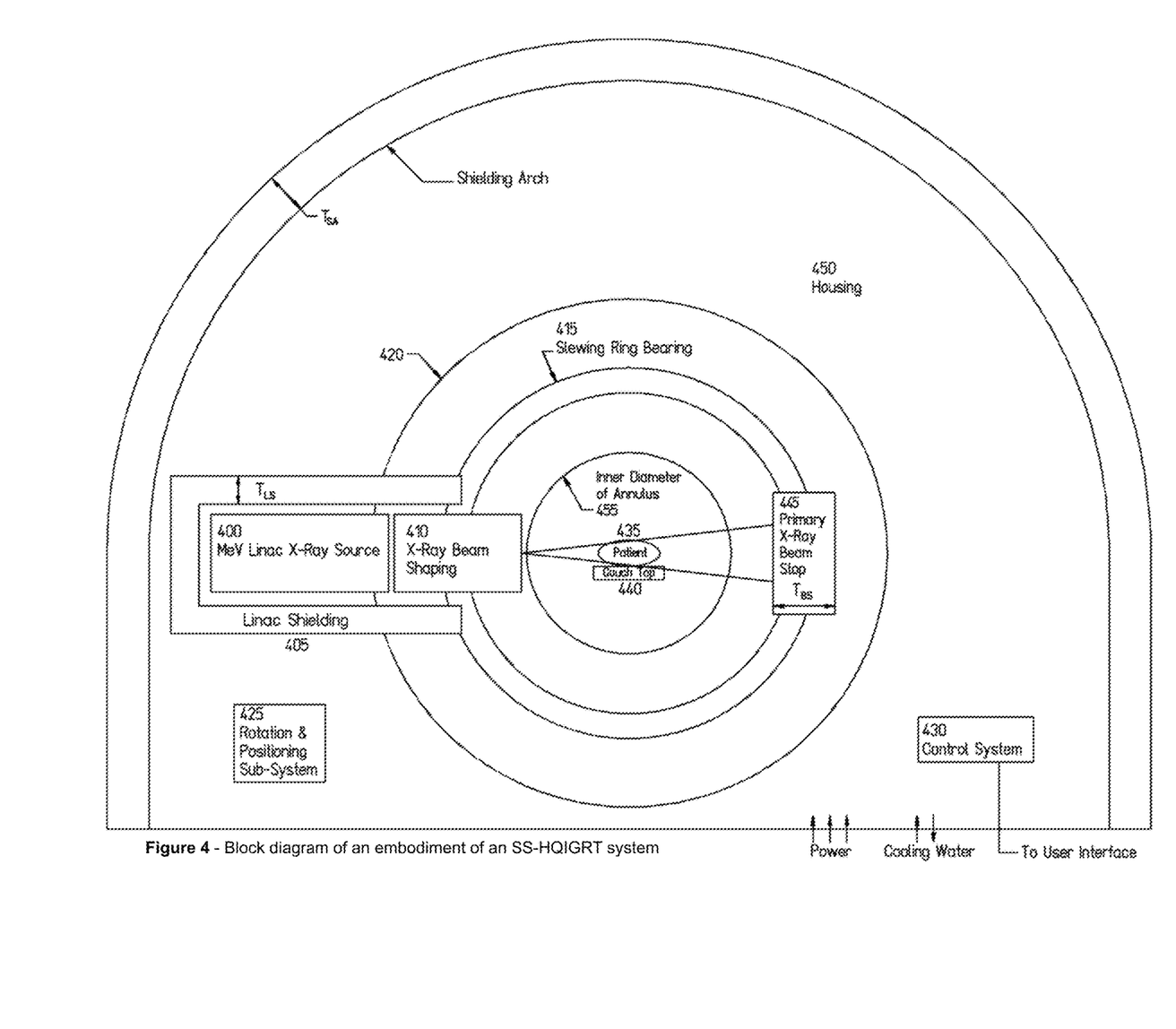
FIG. 4 is a block diagram illustrating the components of an embodiment of a radiation therapy system in accordance with the invention.

In at least some embodiments, the weight of the primary beam stop 140 is nearly the same weight as that of the shielded linac subassembly or treatment head 100, in order that the treatment head and the opposing primary beam stop balance one another when mounted upon the same rotating mechanism, such as a slew ring bearing mechanism [better seen in FIG. 4]. In an embodiment, the primary beam stop weighs approximately 5000 lbs and is substantially constructed of lead, and the shielded linac subassembly also weighs approximately 5000 lbs. Balancing the weights of these two main elements on the rotating structure reduces the amount of force required to maintain the linac orientation in any selected angle around the patient.

The gantry, treatment head and beam stop are designed to work with pre-existing CT scanner couches such that the SS X-ray source, or radiation therapy machine, of the present invention will share the couch with the CT scanner. The treatment head containing the linac and multileaf collimator are configured to not interfere with movement of the CT scanner couch. In some combinations of SS-HQIGRT treatment system and CT scanner, the treatment head of the SS-HQIGRT may only rotate through a portion of a 360 degree arc, in order to avoid interference with the CT scanner couch. This is not a severe limitation, and most cancers treatment plans use little or no angles of orientation of the treatment head below the patient. A preferred embodiment of the invention features a treatment head that travels approximately 270 degrees around the patient, and the treatment head does not travel directly below the patient and couch. In the embodiment of FIG. 2, where the zero degree reference point is at top center, the linac can rotate 270 degrees, from a starting angle of 225 degrees to a final angle of 135 degrees, although the direction of travel of travel is not important. In other embodiments, the ring gantry can permit movement of the treatment head and counter-balancing beam stop through the entire 360 degree arc.

In one embodiment, the multileaf collimator (MLC) 135 allows a 25 cm×25 cm maximum field size at the isocenter, and employs a single energy of 6 MeV. Other field sizes and energies are possible, so long as the shielding is designed with these other parameters in mind. Higher energies and larger areas will generally require more shielding. In an embodiment, the source-to-axis distance can be approximately 85 cm.

Alternative MLC options are also acceptable, for example one that provides 10 mm leaf size at the patient isocenter, or a "micro-MLC" that provides 3 mm leaf size at the patient isocenter. The 10 mm MLC can be used for the majority of treatments, but the micro-MLC option is of interest as it can be used for treatments that benefit from a stereotactic radiosurgery approach (SRS) or a stereotactic body surgery approach (SBRS). Such treatments may include brain metastases, spine lesions, and lung and liver targets with stereotactic precision. A common field size for the standard MLC may be 25 cm×25 cm at the patient isocenter, whereas the field size for the micro-MLC option may be 10 cm×10 cm, or another size.

The combination of features described here will allow a comparatively low cost 6 MeV therapeutic system to be offered, while still enabling treatment of the vast majority of all cancer cases. These benefits result from the present invention because the invention provides all necessary features and precision for most cancers, with the exception of, for example, certain prostate and brain cancers, and also because the integration of the SS X-ray source with a high resolution fan beam CT imaging system allows the resulting SS-HQIGRT system enables to the treating medical team to base their treatment on extremely accurate fan beam CT scans that can be taken immediately before, during, and after a radiation treatment.

Additionally, adding a micro-MLC option to the same machine will allow the treatment of far more than 90% of all cancer cases. Treatment planning and verification can be provided by commercially available existing technology.

In addition to the already described application of a facility using this SS-HQIGRT product as its first radiation oncology system, the present invention is useful to handle overflow from a facility that has one or two high end systems that are at capacity yet where not all of the treated cases require the features of the high end radiation therapy machines. The present invention permits adding an SS-HQIGRT system economically and with minimal facility impact, such that the high end machines can be reserved for cases that require the increased precision or energy levels that such machines offer.

The present invention also makes it possible to minimize the patient trauma that results from hospitalized patients that have to be transported to another facility for radiation therapy. The present invention allows an effective radiation therapy system to be implemented at the local primary care facility such that these patients can be treated on site.

Still referring to FIGS. 1A-1B and 2, the SS X-ray source of the present invention attenuates the primary radiation with a solid arch 115 of lead shielding that will intercept the projection of the radiation beam of maximum useful field size for any available gantry angle. The coverage of the arch can be matched to the amount of rotation possible. Thus, for the embodiment shown in FIG. 2, arches 115 are shown with an opening therebetween since the linac of FIG. 2 only rotates through 270 degrees. In addition, the beam stop 140 is diametrically opposed to the radiation source downstream from the isocenter will attenuate the primary radiation further. In an embodiment, the combined thickness of the arch and beam stop is five Tenth-Value-Layers (TVL) equal to 28.5 cm for 6 MeV photon radiation, although the particular thickness can vary with the energy level of the radiation therapy source and shielding of, for example, 10 TVL can also be desirable for some embodiments. The lead arch is floor-mounted with the inside surface of the arch having a constant distance to the isocenter of the SS-HQIGRT system.

A large portion of the scatter radiation will be absorbed by the lead arch. Any remaining scatter radiation primarily directed towards the head and feet of the patient can be intercepted by a thin wall-mounted steel shield of no more than 2" thickness, which can be easily implemented as a retrofit.

Some of the leakage radiation emanating from the collimating head of the system will be absorbed by the lead shielding that is mounted surrounding the head of the system and will rotate with the Linac. In addition, some of the leakage radiation will be absorbed by the lead arch.

The allowable Radiation level to the public is usually considered to be 100 mrem/year (1 mSv/y) and 5,000 mrem (50 mSv/y) to radiation workers. The overall shielding of the system, i.e., integrated lead arch, head shielding and rotating beam stop, as well as steel plates in the wall of the SS-HQIGRT room, provide enough shielding that the escaping radiation levels that do not exceed these values.

All areas surrounding the SS-HQIGRT room in hospital are assumed to be occupied by non-radiation workers, therefore, a maximum allowable exposure level is often considered to be 100 mrem/year with an occupancy factor of 1.0 (full-time worker). Furthermore, it is assumed that a typical use factor for the machine is 0.1, as the system utilizes all gantry angles and a large portion of the treatments are anticipated to be delivered with Volumetrically Modulated Arc Therapy (VMAT). A utilization factor of the system of 0.1 is assumed as a typical system will only deliver radiation for 10% of the time slot allotted for each patient. A distance of 3.5 m is assumed from the treatment isocenter to the nearest non-radiation worker in the adjacent offices. This will introduce an inverse-square correction factor of 0.081. 5 TVL thickness will be assumed to be used for the primary shield. At a dose rate of 300 MU/min at isocenter is assumed, the instantaneous exposure rate will be 300,000 mrem/min which will be attenuated to 3 mrem/min due to shielding by the lead arch. Applying the use factor, utilization factor, and inverse-square-correction factor yields 0.0024 mrem/min=291.6 mrem/year. This exposure level will be decreased to 100 mrem/year by application of a half TVL in steel.

Any leakage radiation is shielded in a similar way, although for such shielding the use factor will be 1.0. This results in one additional TVL being applied to the shielding.

The integrated shielding provided by this system minimizes the need for significant wall-mounted shielding. Therefore, it is feasible to install this Radiotherapy system in any room with a sufficient footprint and the potential for the described steel plate mounting. It specifically does not require a conventional concrete bunker with wall thicknesses of several feet such as required for higher energy photon beams and larger field sizes.

In certain embodiments, the addition of the beam stop to the system also provides the mechanical benefit of providing a counterweight to the treatment head with its separate leakage shielding. It can be of benefit to nearly match the weight of the beam stop with the weight of treatment head, so that the two are balanced with respect to the mechanical load-bearing ring or gantry about which both rotate. The balance of the rotating part of the system, with its two independent shields, can be of benefit for the purpose of precision location of the treatment beam, and can be of benefit in minimizing the mechanical power required to rotate and stabilize the machine.

Figure 3:
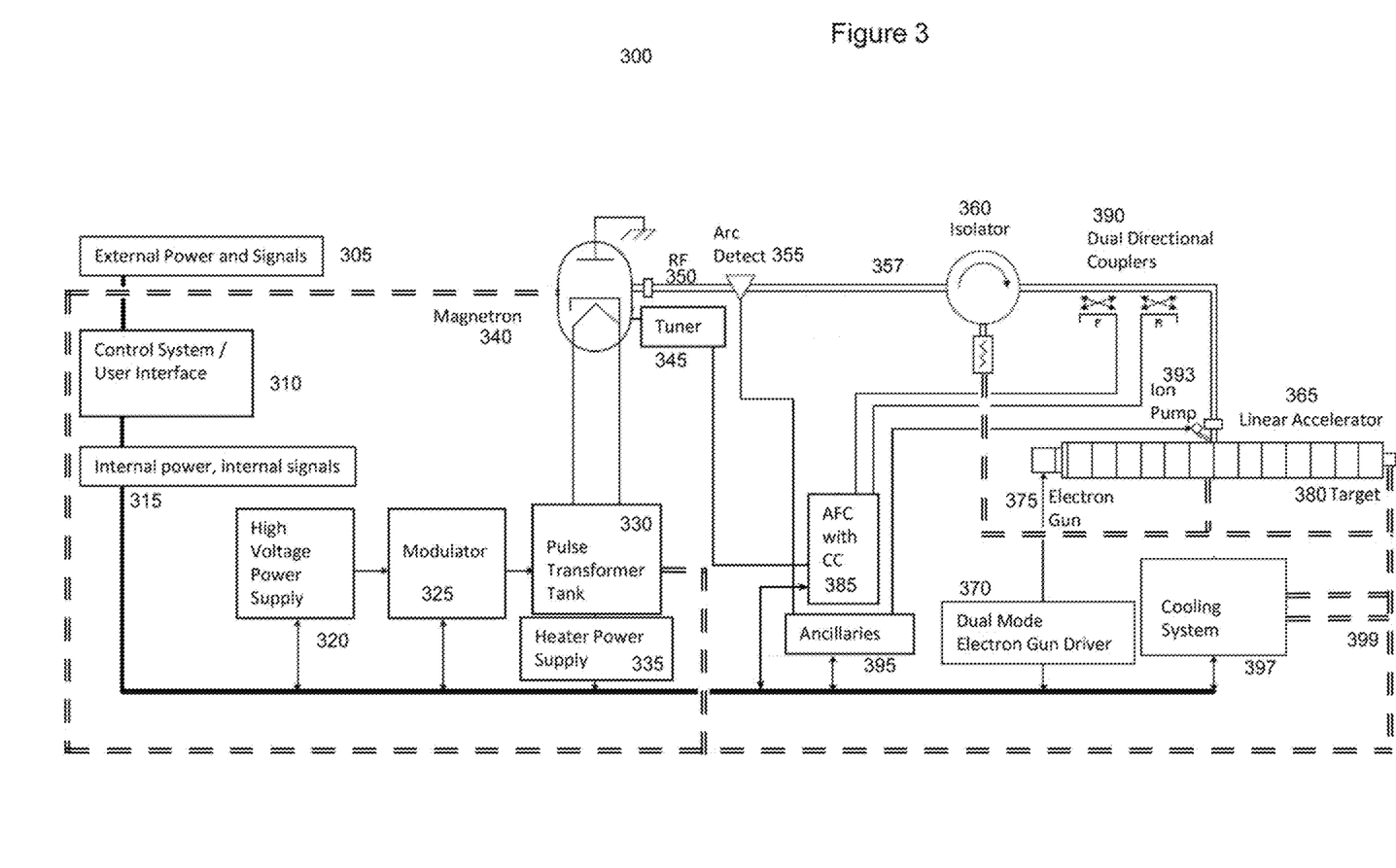
FIG. 3 is a block diagram of the electrical system of an X-ray source in accordance with an embodiment of the invention.

Referring next to FIG. 3, an X-ray scanning system according to an embodiment of the invention is shown in block diagram form at 300. In such an embodiment, external power and signals 305 are received by a control processor 310. Included among the external signals are, typically, one or more trigger signals indicating that the user desires to scan an object, for example a cargo container on a vehicle passing before the scanning system. The control processor 310 controls, directly or indirectly, the operation of the remaining functional blocks shown in FIG. 3 by virtue of signals sent on internal bus 315, which, for simplicity, is shown combined with internal power.

In response to the trigger signal(s), the control processor 310 sends, depending upon the implementation, a plurality of signals to initiate generation of an X-ray pulse. In particular, the processor 305 sends control signals to a high voltage power supply 320 and an associated modulator 325 which receives the output from the supply 320. The supply 320 can be, for example, a Lambda LC1202. The output of the modulator 325 supplies a high voltage output to a pulse transformer 330, typically immersed in an insulating tank for purposes of electrical isolation. An aspect of the modulator is that can vary the voltages from one pulse to the next, and can operate at pulse durations of 2.5 μsec or less, to permit operation at 400 pulses per second. The modulator may incorporate a pulse-forming network or PFN. A heater power supply 335 is associated with the tank and supplies the magnetron 340 or other suitable RF power source. The pulse transformer 330 supplies high energy pulses, for example 30-50 kV at 100-110 amps, to a magnetron 340 or other suitable RF power source. One suitable magnetron is the e2V model MG5193, which has an output of 2.6 MW at the normal S band frequency of 2.998 GHz. Another is the MG7095, also from e2V. Still other similar magnetrons are available from NJRC. The specific magnetron frequency is controlled by a mechanical tuner 345.

The magnetron 340 outputs an RF power pulse, indicated at 350, at the frequency determined by the tuner 345. As explained in greater detail below, the pulses received by the magnetron can be of different, pre-selected voltage and currents, thus causing the magnetron to output pulses of different, pre-selected RF powers, for example, pulses of 40 kV and 45 kV at 100 amps and 110 amps, respectively. Because of the nature of the magnetron, the different powers of the RF pulses also affect the frequency of the output pulse, again as explained in greater detail below. The RF power pulses pass through an arc detector 355, an isolator 360, and then to a linear particle accelerator (sometimes "linac" hereinafter) 365. Suitable isolators are available from Ferrite Incorporated. Conventional S-band waveguide 357 is used between magnetron and linac. Depending upon the requirements of the particular linac, for example of the type shown in FIG. 2, the pulses received from the transformer 330 can be in the range of, for example, 35-50 kV. The linac 365, which typically has an effective Q in the range of 2000-4000, but in any event less than 5000, receives the RF pulse. The tuner 345 is adjusted so that the RF pulses from magnetron 340 are within the resonance bandwidth of the linac 365. The pulses from the magnetron are, in an embodiment, substantially in the range of 2.5 MW, or between 2.0 MW and 3.0 MW.

In the embodiment of FIG. 3, the control processor 310 sends a control pulse to the modulator 325, and it sends a synchronized control pulse to a dual mode electron gun driver block 370. The timing of these control pulses may be individually optimized. The dual mode electron gun driver block 370, explained in greater detail hereinafter in connection with FIG. 5, drives an electron gun 375, the cathode of which is within the vacuum envelope of the linac 365. The gun 375 can be a triode gun design. In an embodiment, the pulses of beam current from electron gun 375 launch electrons into the cavities of the linac. The cathode voltage is substantially in the range of −10 to −20 kV. In an embodiment it is −20 kV. By timing the electron pulses at the linac to optimally synchronize with the electric field created by the RF pulses from the magnetron, as discussed in greater detail hereinafter, the electrons are accelerated by the linac to a desired energy level, typically in the range of two to ten or more MeV with, for at least some embodiments, a separation between the energy levels of approximately 1 MeV or more between sequential pulses in a rapidly pulsed ABABABAB pattern. The pulses are directed toward a target 380, for example tungsten, which, when hit with the pulse of accelerated electrons, emits pulses of X-rays. As discussed below in connection with FIGS. 3 and 4A-4E, the RF pulses are, in an embodiment, somewhat longer in duration than the electron gun pulses, such that the RF pulses can be thought of as creating an envelope within which the beam current pulses occur. To control dose, the duration of the beam current is selected by the control system 310, or can be pre-set during manufacture.

Because the transmission characteristics of the linac and magnetron vary with temperature and other environmental factors, an AFC circuit 385 detects forward and reflected power from the linac, using dual directional couplers 390, and in turn controls the tuner 345 to ensure a continuing match between the linac and the magnetron in a manner known to those skilled in the art.

In addition, ancillaries 395 connect to the arc detector 355 and an ion pump 393 that feeds the linac 365, both in a manner known to those skilled in the art. Finally, a cooling system 397 cools portions of the system in a manner known in the art, for example, the modulator, the pulse transformer tank, the linac, the target, and the isolator, as indicated by the dashed line 399. Suitable cooling systems are available from OptiTemp, and can be chosen dependent upon temperature and cooling requirements of the linac system.

Referring next to FIG. 4, the features of an embodiment of an SS X-ray source in accordance with the invention can be better appreciated. In particular, a linac X-ray source 400 is surrounded by linac shielding 405. A beam shaping unit 410, such as a multi-leaf collimator, is provided at the exit aperture of the linac 400. The linac and associated shielding travel along a slew ring bearing 415 of a ring gantry 420 which forms the electro-mechanical part of the positioning system, with the movement of the linac along the bearing track controlled by rotation and positioning subsystem 425 and control system 430. Alternatively, the treatment head and beam stop can both be mounted on a rotating frame where the frame is supported by the slew ring bearing 415. The frame is not shown in FIG. 4, for clarity, but is shown at 530 in FIGS. 6 and 7. In some embodiments such an arrangement is preferred.

The linac output aperture and beam shaping unit direct the beam toward a patient 435 positioned on a couch 440, typically provided by an adjacent CT scanner or similar device. Positioned diametrically opposed to the linac 400 is a primary beam stop 445, which moves with the linac 400 as discussed above. A housing 450 for the bearing track (shown better in FIGS. 5-7) typically creates an annulus 455 through which the couch passes during the treatment of the patient. In an embodiment, the shielding arch 460 is floor mounting and its upper portion is substantially circular to match the substantially circular rotation of the treatment head 100 and beam stop 445. Connections to power, cooling water, and a user interface are all provided in a manner known to those skilled in the art.

The thicknesses of the various shieldings are $T_{BS}$, which is the thickness of the beam stop, $T_{LS}$, which is the thickness of the walls of the shielding directly around the linac source, and $T_{SA}$, which refers to the thickness of the walls of the shielding arch.

In order to control an MeV radiation oncology system such as the present invention for the purpose of treating a patient, a radiation therapy plan file is provided to the system operator in standardized format such as DICOM. The radiation therapy plan file is typically provided by a conventional treatment planning system, i.e., PROWESS Puma, Philips Pinnacle, or CMS Monaco. This file is imported by the control computer of the MeV radiation oncology system, such as control system 310 of the present invention and the control computers of similar prior art devices. Typically included in the radiation therapy plan file are the following parameters, indexed in time: gantry position, collimator position, MLC leaf positions, dose rate, total dose delivered, and gantry speed.

These parameters are used to drive the respective components of the radiation oncology system to the required position or value. In the case of VMAT, the change in parameters is continuous (constantly changing gantry position, collimator position, etc.) The actual values for these parameters are typically measured by potentiometers, optical encoders, or other conventional means for position measurement. Dose rate is typically measured by the signal from the dose chamber. Gantry speed is calculated by the measured rate of change of the gantry, for example degrees traveled per unit time.

If a deviation is detected in the actual value from the required value, a real-time correction is typically implemented to compensate for this deviation. Typically, if this feedback loop and real-time correction can be completed in approximately 20 ms, any deviation is deemed clinically acceptable. In the case of total dose, the radiation is interrupted or stopped when this dose has been reached, to avoid overexposing the patient.

Unlike the prior art, when the present invention is used to treat a patient, and is physically positioned adjacent to a fan beam CT scanner, the original DICOM Image data file can be compared against a fan beam CT scan that is taken before every treatment. This is a substantial advantage because the radiation treatment plan is typically created from a diagnostic fan beam CT scan, and so comparing with the fan beam CT scan taken with the fan beam CT scanner adjacent the present invention, where the patient remains on the same couch for both the CT scan and the radiation treatment, provides the treatment team with a much higher quality correlation between the original treatment plan images and the images taken on the day of treatment. This permits more accurate and reliable positioning of the patient. This is in contrast to a typical radiation therapy machine, such as a Varian Truebeam or an Elekta Precise or others, which include cone beam CT scanning as imaging on their systems. It is well understood in the art that images from cone beam CT scanner are inferior to images from a fan beam CT scanner.

Figure 5:
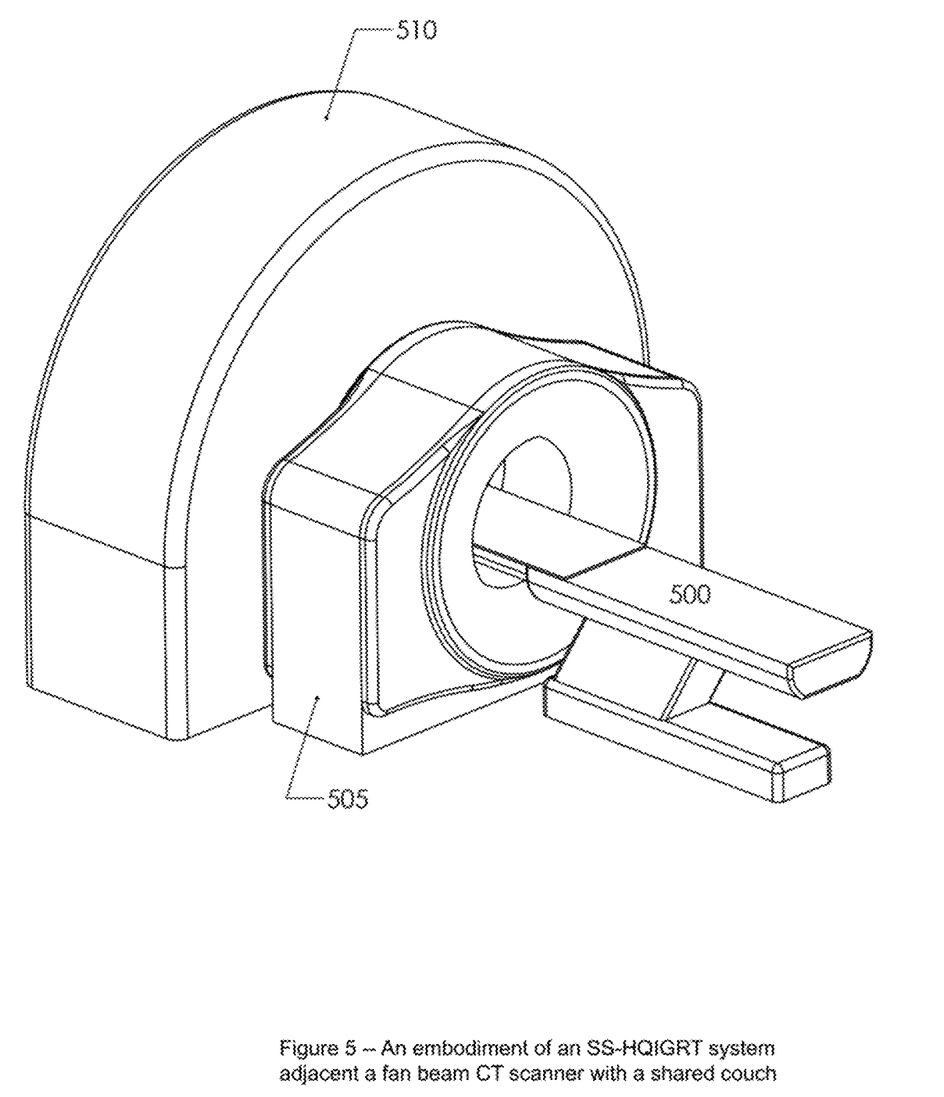
FIG. 5 is a perspective view of a radiation therapy system in accordance with the present invention, juxtaposed with a fan beam CT scanner so that the overall system substantially integrates a fan beam CT scanner with a SS_HQIRT system, in accordance with another aspect of the invention.
Figure 6:
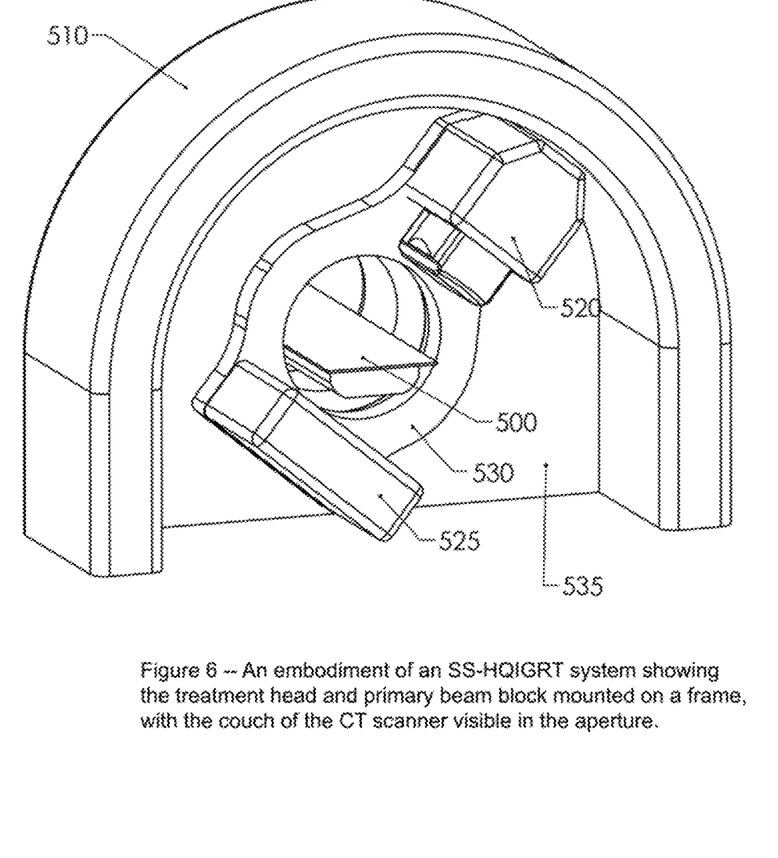
FIG. 6 is a perspective view of the system of FIG. 5 showing the shielding arch and primary beam block of the X-ray source of the present invention relative to the couch of the CT scanner, where the couch is shared with both systems.
Figure 7:
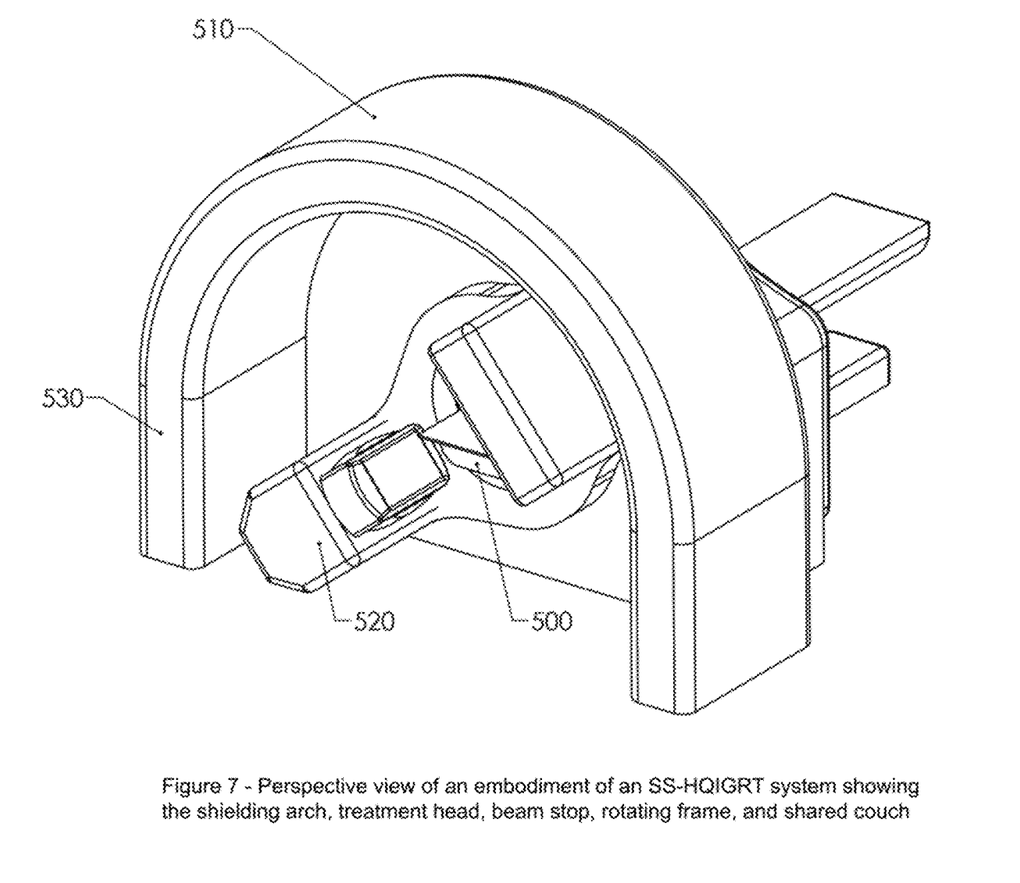
FIG. 7 is a further perspective view of the system of FIG. 5, with the radiation treatment head rotated for better viewing and with the primary beam block removed.
Figure 8A:
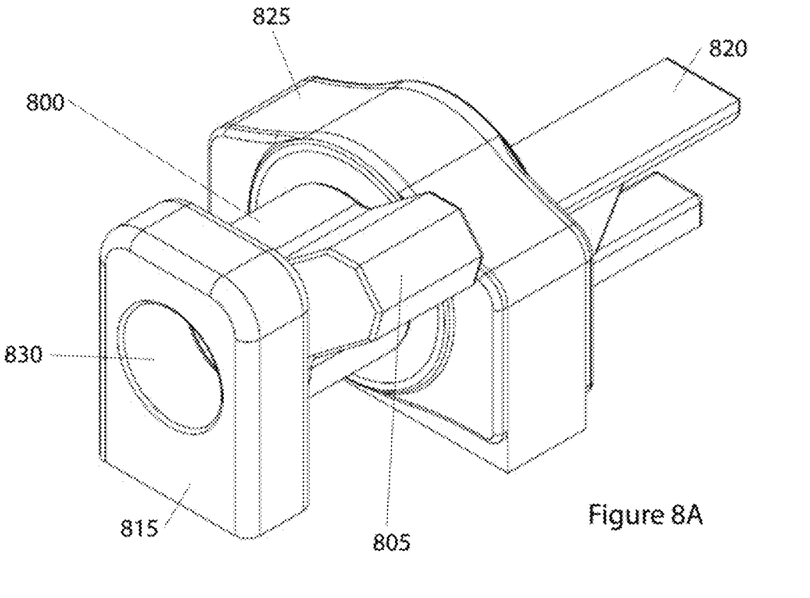
FIGS. 8A-8B show a perspective and front elevational view, respectively, of an alternative embodiment of the invention juxtaposed with a fan beam CT scanner, and wherein the shielding arch of the embodiment of FIGS. 5 and 6 is replaced with a shielding cylinder located more proximately to the patient.
Figure 8B:
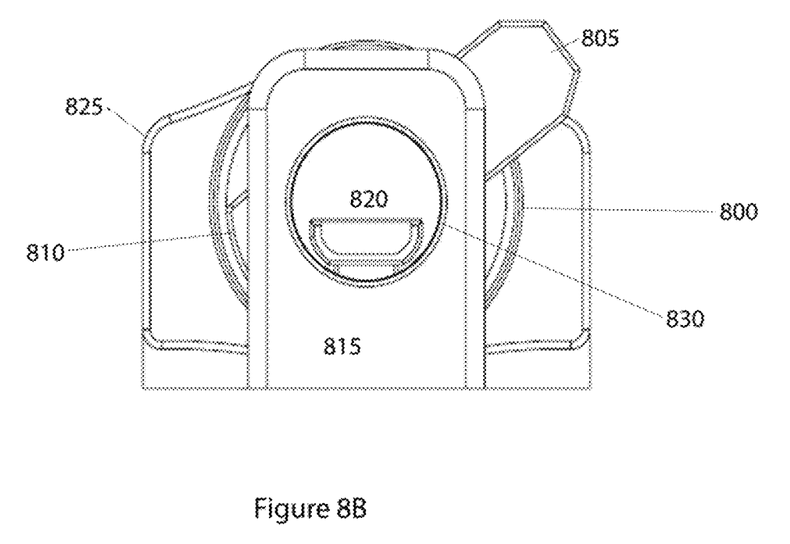

Referring next to FIGS. 5-7, various perspective views of an SS_HQIRT system in accordance with the invention can be appreciated. Further, the juxtaposition of the SS X-ray source described in FIGS. 1-4 with a fan beam CT scanner or equivalent high quality imager can also be appreciated. In particular, the patient table or couch 500 can be seen to be mounted so that it passes through an annulus of a high quality imager 505 such as a fan beam CT scanner. Adjacent to the imager 505 is an SS X-ray source 510 in accordance with the invention, with only the outer housing 515 of the arch shown in FIG. 5. The linac-based treatment head 520 and associated beam stop 525 can be seen in FIGS. 6 and 7. The frame 530 upon which the treatment head and beam stop are mounted is also shown, with the frame riding on a slew ring bearing, shown at 415 in FIG. 4, mounted in the supporting wall or housing 535.

Figure 9A:
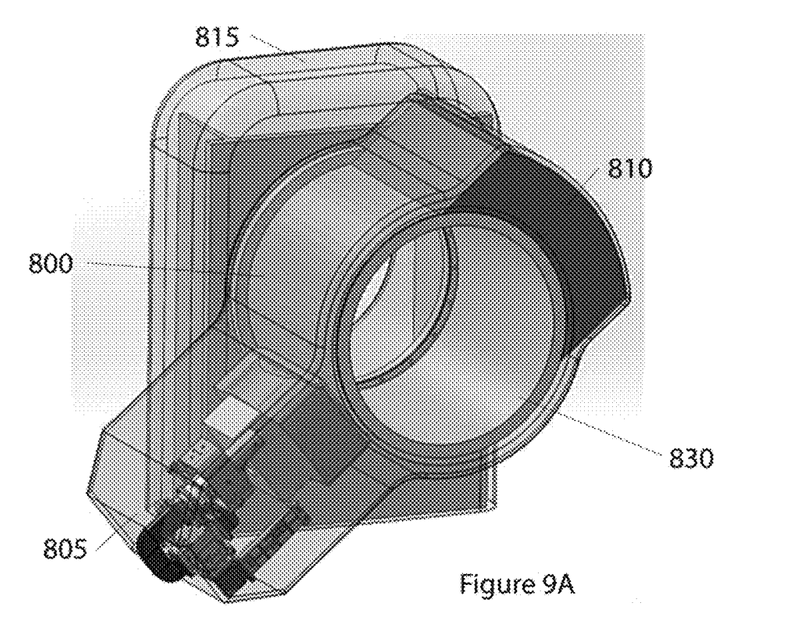
FIG. 9A shows in perspective view the embodiment of FIGS. 8A-8B separated from the CT scanner, thus showing the shielding cylinder in greater detail and with the linac and counterweight shown exposed for clarity.
Figure 9B:
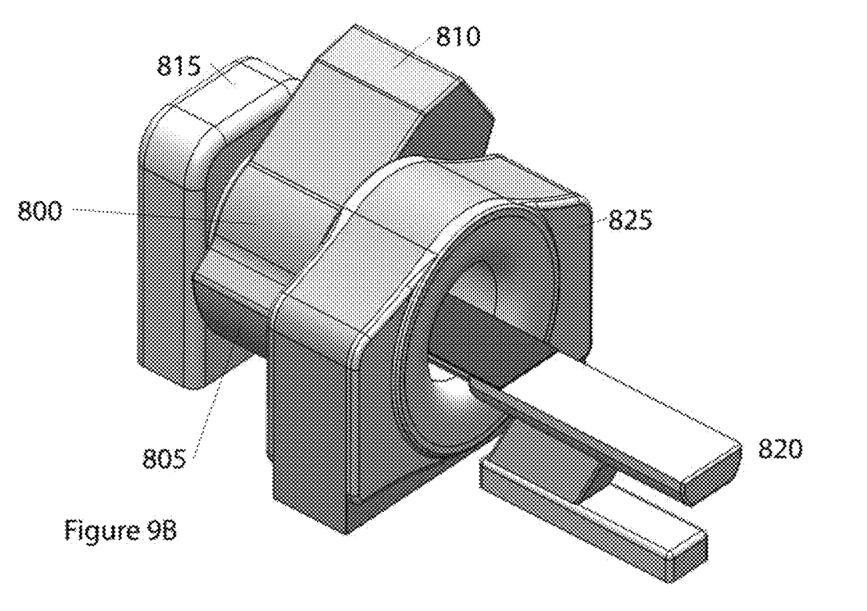
FIG. 9B shows in perspective view the embodiment of FIGS. 8A-8B integrated with the CT scanner and showing the common patient couch in relation to the scanner.

Referring next to FIGS. 8A-8B and 9A-9B, a further alternative embodiment can be better appreciated, in which the shielding arch of FIGS. 5 and 6 is replaced with a shielding cylinder 800, perhaps best appreciated from FIG. 9A. A linac-based treatment head 805 and opposing beam-stop or beam block 810 are supported on the shielding cylinder 800, and the gantry assembly of the head, beamstop and cylinder are rotatably mounted on a supporting frame or wall 815 by means of a slew ring bearing substantially as shown at 415 in FIG. 4. The shielding cylinder 800 can comprise, for example, steel shielding of approximately 3" thick, while the beam block 810 is, in an embodiment, lead and provides 10 TVL shielding. As shown best in FIGS. 8A-8B, a patient couch 820 for a CT scanner 825, preferably a fan beam CT scanner although not necessarily in all embodiments, extends through a tunnel 830 in the cylinder 800 and continuing through the wall 815, in alignment with the corresponding tunnel in the CT scanner 825. Appropriate housings enclose each of these components as necessary, and the tunnel 830 inside the housing is, in an exemplary embodiment, approximately 80 cm in diameter.

As noted previously, the fan beam CT scanner can be any of several readily available devices, such as the Siemens Sensation, the GE Lightspeed, the Philips MX, or other fan beam CT scanner capable of 8 to 16 or more slices. The shielding cylinder 800 offers the benefit of being closer to the patient and thus making it more effective as a radiation shield for a given weight. As with the arch, the purpose of the cylinder 800 is to capture radiation scattered from the patient and from the primary beam block, thereby protecting personnel operating the equipment or otherwise present. Such personnel are typically in the vicinity of the equipment but a reasonable distance away, with that distance determined at least in part by the effectiveness of the shielding. Similar to the embodiment of FIGS. 5 and 6, the shielding cylinder 800 of FIGS. 8A-8B together with the beam stop 810 combine to provide shielding of ten Tenth-Value-Layers although the amount of shielding can vary with the implementation.

As with the earlier-described embodiments, the embodiment of FIGS. 8A-9B offers substantially vaultless image-guided radio therapy, thus significantly simplifying the installation of such treatment capabilities in hospitals or other facilities that do not have vaults of the type typically required of conventional treatment systems. In a world where 80% or more of the population is served by less than 3,000 such treatment systems, while less that 15% of the world is served by more than 5,000 such systems, the value of the present invention to provide radiotherapy to patient populations without prior access cannot be underestimated. In addition, the present invention can be retrofitted to an existing CT scanner without the need to construct a vault around the combined system.

In an exemplary embodiment, the present invention can provide IGRT with 6 MeV over a 25 cm field, with a 1 cm MLC. The percent depth does at 10 cm over a 10×10 field can be in the range of 61.5%±1%, with a maximum dose depth of approximately 1.5 cm±0.1 cm, a beam flatness (with interlock associated) of 3.0% and a beam symmetry (again with interlock associated) of 2.0%. The dose rate at iso can be approximately 3 Gy/min to 6 Gy/min with a maximum field size of 25 cm×25 cm at iso, where the MLC leaf width is 10 mm and the maximum leaf speed is about 3.0 cm/sec. Such a system can have an isocenter positioning accuracy of approximately 1.0 mm with a maximum gantry speed of 6 degrees per second and a gantry positioning accuracy of 0.1 degrees. The system can deliver either IGRT or VMAT, at a source to axis distance (SAD) of about 85 cm, during circular motion of the linac. As noted previously, the rotation of the linac typically extends through 270 degrees, with the sector below the couch excluded from the rotation range in at least some embodiments. In such an implementation, leakage radiation can be approximately 0.005% of the exposure rate at the isocenter.

Figure 10:
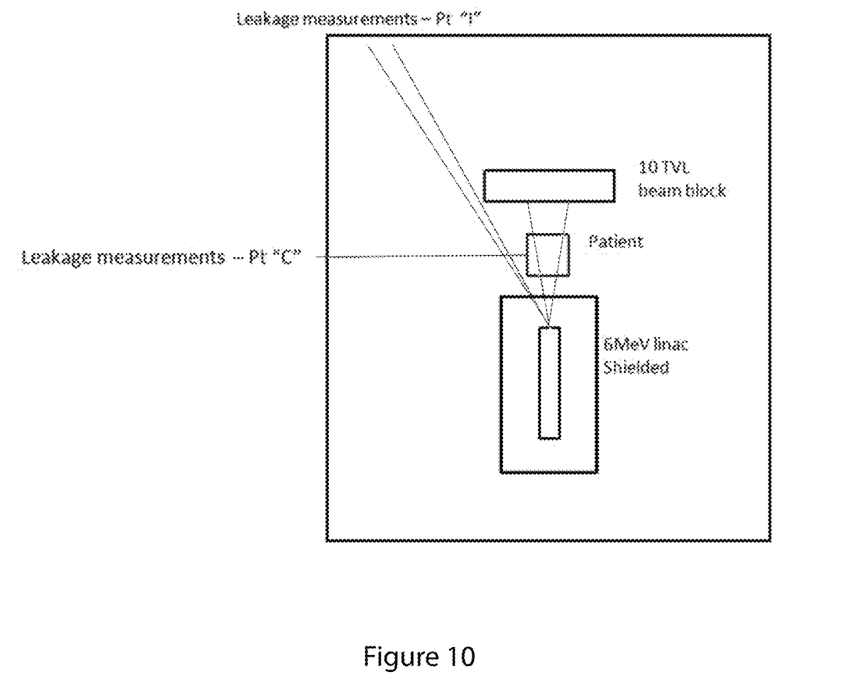
FIG. 10 shows an exemplary arrangement of key components to facilitate a calculation of expected radiation leakage from the present invention such as shown in FIGS. 8A-8B.

FIG. 10 shows an arrangement of the present invention suitable for determining anticipated radiation exposure to the operator and others in the vicinity with a treatment room having 3" steel shielding at selected strategic locations. In most implementations such shielding will not be needed for the entire room, and the specific locations requiring such extra shielding can be determined upon implementation of the particular IGRT or VMAT system. At point C shown in FIG. 10, the anticipated radiation along the longitudinal (patient) axis at 2.8 meters from the isocenter, without shielding, is 145 mR/hr, but with properly located three inch steel shielding drops to 3.6 mR/hr. At point I in FIG. 10, radiation anticipated closest to cax and not blocked by the beam stop, at a distance of 3.66 meters from the isocenter, is 330 mR/hr, but with three inch steel shielding for the room drops to 23 mR/hr. Thus, annual exposure can be calculated to be 460.8 mR/year at point C and 294.4 mR/year at point I, based on 2,000 working hours per year with a clinical utilization factor of 0.1, an inverse-square correction factor of 0.64 and a beam rotation use factor of 0.1. It can be appreciated by those skilled in the art that these numbers are below 10% of the maximum annual permissible exposure of 5,000 mR. It will thus be appreciated that the present invention avoids the need to construct the conventional vault of several feet of concrete, or extensive lead shielding. As a result, the present invention offers significantly improved performance and usability in that it enables facilities that previously could not accommodate IGRT to offer treatment to patients requiring such medical treatments.

Having fully described in detail several embodiments of the invention, those skilled in the art will recognize from the teachings herein numerous alternatives and equivalents that do not depart from the scope of the invention. As a result the invention is not to be limited to the foregoing description but only by the appended claims.

We claim:

1. An image-guided radiotherapy system not requiring a conventional concrete vault to protect public areas from excessive radiation exposure comprising
 a frame having an orifice adapted to permit passage therethrough of a couch on which a patient is positioned,
 a gantry assembly rotatably mounted on the frame, the gantry assembly comprising a shielding cylinder having an orifice therethrough in alignment with the orifice in the frame, and
 the shielding cylinder comprising a shielding arch and having affixed thereto a linac-based, radiation-shielded treatment head configured to provide radiotherapy proximate to an isocenter, and
 a radiation-shielding beamstop positioned angularly opposite the treatment head to absorb radiation from the treatment head, wherein the radiation shielding provided by the combination of the shielding arch, the treatment head and the beamstop provide sufficient shielding that the radiation emitted during treatment at approximately 6 MeV in doses in a range of approximately 3 Gy/min to approximately 10 Gy/min is less than approximately 300 mrem/year at a distance of at least 3.5 meters from the isocenter.

2. The radiotherapy system of claim 1 wherein the frame is configured to be positioned immediately adjacent a fan beam CT scanner having a couch.

3. The radiotherapy system of claim 1 wherein the linac-based treatment head provides radiotherapy of approximately 6 MeV energy levels at approximately one meter from the linac.

4. The radiotherapy system of claim 1 wherein the shielding cylinder places the shielding proximate to the isocenter.

5. The radiotherapy system of claim 4 wherein the placement of the shielding relative to the isocenter increases the effective dose rate.

6. The radiotherapy system of claim 5 wherein the treatment head defines a radiation source, and the distance from the radiation source to the isocenter is approximately 85 centimeters with a treatment field of approximately 25 cm by 25 cm at the isocenter.

7. The radiotherapy system of claim 5 wherein the dose rate at the isocenter is in the range of approximately 3 Gy/min to 6 Gy/min with a field size having a maximum of approximately 25 centimeters by 25 centimeters at the isocenter with an MLC having a leaf width of approximately 10 millimeters and a maximum leaf speed of approximately 3 centimeters per second.

8. The radiotherapy system of claim 1 wherein the radiation source travels a substantially circular beam path.

9. The radiotherapy system of claim 1 wherein the treatment head can rotate approximately 270 degrees around the couch and excludes a region below the couch.

10. The radiotherapy system of claim 1 wherein the treatment head can rotate 360 degrees around the couch.

11. The radiotherapy system of claim 1 wherein the radiation shielding yielding less than approximately 300 mrem/year at a distance of at least 3.5 meters from the isocenter is achieved without coupling the shielding cylinder, the treatment head and the beamstop.

12. An image-guided radiotherapy (IGRT) system comprising
 a shielding arch configured to block x-ray radiation, and
 a gantry rotatably mounted to a frame, the gantry having thereon a radiation-shielded linac-based treatment head for delivering radiotherapy proximate to an isocenter and a radiation-shielded beamstop diametrically opposed thereto, with a tunnel passing through both the gantry and the frame configured to receive a couch bearing a patient when the radiotherapy system is juxtaposed adjacent a CT scanner with the tunnel in alignment with a tunnel in the CT scanner, wherein the radiation shielding provided by the combination of the shielding arch, the treatment head and the beamstop provide sufficient shielding that the radiation emitted during treatment at approximately 6 MeV in doses in a range of approximately 3 Gy/min to approximately 10

Gy/min is less than approximately 300 mrem/year at a distance of at least 3.5 meters from the isocenter.

13. The radiotherapy system of claim 12 wherein the beamstop weighs approximately the same as the treatment head.

14. The radiotherapy system of claim 12 wherein the treatment head can rotate approximately 270 degrees around the couch and excludes a region below the couch.

15. The radiotherapy system of claim 12 wherein the treatment head can rotate 360 degrees around the couch.

16. The radiotherapy system of claim 12 further comprising a multileaf collimator (MLC) that provides a leaf size at the isocenter ranging from approximately three millimeters to approximately ten millimeters.

17. The radiotherapy system of claim 16 configured to provide IGRT with 6 MeV over a twenty-five centimeter field with a ten millimeter MLC.

18. The image-guided radiotherapy system of claim 1 wherein the shielding cylinder and the beamstop combine to provide shielding of approximately five Tenth-Value-Layers.

19. A vaultless image-guided radiotherapy system comprising a frame having an orifice therethrough adapted to permit passage of a couch on which a patient is positioned, a gantry assembly rotatably mounted on the frame, the gantry assembly comprising a shielding cylinder having a tunnel therethrough in alignment with the orifice in the frame, and the shielding cylinder having affixed thereto a linac-based, radiation-shielded treatment head configured to provide radiotherapy, and a beamstop positioned angularly opposite the treatment head to absorb radiation from the treatment head, wherein the shielding cylinder is comprised of steel and the beamstop is comprised of lead in sufficient thickness that the combination of the shielding cylinder, radiation-shielded treatment head and beamstop cooperate to shield radiation from the treatment head such that radiation along a longitudinal (patient) axis at approximately 2.8 meters from an isocenter defined by the treatment head is reduced to approximately 3.6 mR/hr.

20. The vaultless image-guided radiotherapy system of claim 19 wherein leakage radiation is no more than approximately 0.005 percent of the exposure rate at the isocenter.

* * * * *